United States Patent
Kaufmann et al.

(10) Patent No.: US 8,668,729 B2
(45) Date of Patent: Mar. 11, 2014

(54) STENT FOR IMPLANTATION IN A BLOOD VESSEL, ESPECIALLY IN THE REGION OF THE AORTIC ARCH

(75) Inventors: Ralf Kaufmann, Rangendingen (DE); Rainer Lesmeister, Reutlingen (DE); Hardy Müller, Bisingen (DE); Michael Braun, Backnang (DE); John Geis, Bad Zwischenahn (DE)

(73) Assignee: Jotec GmbH, Hechingen (DE)

(*) Notice: Subject to any disclaimer, the term of this patent is extended or adjusted under 35 U.S.C. 154(b) by 1147 days.

(21) Appl. No.: 11/352,590

(22) Filed: Feb. 10, 2006

(65) Prior Publication Data

US 2006/0195177 A1 Aug. 31, 2006

Related U.S. Application Data

(63) Continuation of application No. PCT/EP2004/008916, filed on Aug. 10, 2004.

(30) Foreign Application Priority Data

Aug. 12, 2003 (DE) .................................. 103 37 739

(51) Int. Cl.
*A61F 2/06* (2013.01)

(52) U.S. Cl.
USPC ........................................................ 623/1.13

(58) Field of Classification Search
USPC ......... 623/1.11, 2, 1.13, 1.15, 1.16, 1.18, 1.2, 623/1.12, 1.17, 1.19, 1.21
See application file for complete search history.

(56) References Cited

U.S. PATENT DOCUMENTS

| | | | | |
|---|---|---|---|---|
| 5,591,195 A | * | 1/1997 | Taheri et al. | 623/1.11 |
| 5,676,696 A | * | 10/1997 | Marcade | 623/1.35 |
| 5,733,325 A | * | 3/1998 | Robinson et al. | 623/1.11 |
| 5,800,515 A | * | 9/1998 | Nadal et al. | 623/1.15 |
| 5,800,521 A | * | 9/1998 | Orth | 623/1.23 |
| 5,843,167 A | * | 12/1998 | Dwyer et al. | 623/1.14 |
| 6,030,414 A | | 2/2000 | Taheri | |
| 6,071,307 A | * | 6/2000 | Rhee et al. | 623/1.13 |

(Continued)

FOREIGN PATENT DOCUMENTS

| | | |
|---|---|---|
| DE | 100 65 824 | 7/2002 |
| EP | 1 075 825 | 2/2001 |

(Continued)

OTHER PUBLICATIONS http://www.thefreedictionary.com/distinct, dictionary definition of distinct.*

(Continued)

*Primary Examiner* — Thomas McEvoy
*Assistant Examiner* — David Eastwood
(74) *Attorney, Agent, or Firm* — Morrison & Foerster LLP

(57) ABSTRACT

A stent for implantation in a blood vessel is disclosed, especially in the region of the aortic arch. The stent is comprising rings which are disposed successively in the stent's longitudinal direction and which are made up of meandering circumferential supports. The stent further comprises a prosthesis material which is fixed to the rings and which connects them, thereby forming a hollow cylindrical body with a jacket which is substantially closed on the circumference thereof. At least one connecting support is provided between the last ring and the penultimate ring at the proximal end of the stent and connects these two rings to one another.

21 Claims, 8 Drawing Sheets

(56) References Cited

U.S. PATENT DOCUMENTS

| | | | |
|---|---|---|---|
| 6,123,723 A * | 9/2000 | Konya et al. | 623/1.11 |
| 6,200,336 B1 * | 3/2001 | Pavcnik et al. | 623/1.15 |
| 6,319,278 B1 * | 11/2001 | Quinn | 623/1.13 |
| 6,355,056 B1 * | 3/2002 | Pinheiro | 623/1.13 |
| 6,524,335 B1 * | 2/2003 | Hartley et al. | 623/1.13 |
| 2002/0156522 A1 * | 10/2002 | Ivancev et al. | 623/1.13 |
| 2003/0120331 A1 * | 6/2003 | Chobotov et al. | 623/1.13 |

FOREIGN PATENT DOCUMENTS

| | | |
|---|---|---|
| EP | 1 245 202 | 10/2002 |
| EP | 1 336 393 | 8/2003 |
| WO | WO-97/09945 | 3/1997 |
| WO | WO-99/29262 | 6/1999 |
| WO | WO-99/39663 | 8/1999 |
| WO | WO-99/43378 | 9/1999 |
| WO | WO-01/56500 | 8/2001 |

OTHER PUBLICATIONS

Translation of the International Preliminary Report on Patentability for PCT/EP2004/008916, mailed Aug. 1, 2006, 5 pages.

International Search Report for PCT/EP2004/008916, mailed on Dec. 17, 2004, 3 pages.

* cited by examiner

STENT FOR IMPLANTATION IN A BLOOD VESSEL, ESPECIALLY IN THE REGION OF THE AORTIC ARCH

CROSS-REFERENCE TO RELATED APPLICATIONS

This is a continuation application of International Patent Application PCT/EP2004/008916, filed on Aug. 10, 2004, designating the United States and published in German as WO 2005/013854 A1, which claims priority to German application number 103 37 739.5, filed on Aug. 12, 2003. The contents of these documents are incorporated herein by reference.

TECHNICAL FIELD

The present invention relates to a stent for implantation in a blood vessel, especially in the region of the aortic arch, with rings which are disposed successively in its longitudinal direction and which are made up of meandering circumferential supports, and with a prosthesis material which is fixed to the rings and which connects them, said prosthesis material forming a hollow cylindrical body with a jacket which is substantially closed on the circumference.

These endovascular stents are implanted for treatment of aneurysms in arteries. An aneurysm is understood as a widening or bulging of an arterial blood vessel as a consequence of congenital or acquired lesions of the vessel wall. The bulge can affect the vessel wall as a whole or, in what is called a false aneurysm, blood can flow from the lumen of the vessel in between the layers of the vessel wall and can tear these apart from one another. Nontreatment of an aneurysm may lead to a rupture of the artery in advanced stages, after which the patient may suffer internal bleeding.

Although aneurysms often occur in the area of the abdominal aorta (aorta abdominalis) or thoracic aorta (aorta thoracica), an aneurysm may, however, also occur in the area of the ascending or descending branch of the aorta (aorta ascendens and aorta descendens). The ascending branch of the aorta is directly connected to the heart. Starting from the aortic root (sinus aortae), the ascending branch extends upward in a slightly curved shape away from the heart and merges into the aortic arch (arcus aortae). The vessels of the head, among others the left and right carotid arteries, branch off in the area of the aortic arch. The aortic arch follows a curve of approximately 180 degrees with a very narrow radius and connects the ascending branch of the aorta to the descending branch.

BACKGROUND ART

By way of example reference is made to document DE 100 65 824 A1, disclosing a stent for implantation in the ascending branch of the aorta. This prior art stent has a hollow cylindrical body which is open in the longitudinal direction for the passage of blood and which has a wall formed by a mesh structure. The body of the known stent is adapted to the anatomical shape of the aortic root and has a configuration widening in a concave shape. At its proximal end directed toward the heart, narrow fixing elements are distributed on the stent in the circumferential direction. At its distal end extending into the aortic arch, the body of the known stent is, as it were, cut off obliquely so that, on its circumferential area situated away from the vessels of the head in the implanted state, the stent has a greater longitudinal extent than it does on the opposite circumferential area. This means that the vessels of the head which branch off from the aortic arch are not covered by the stent.

The prior art stent has proven easy to implant in the area of the ascending aorta. Because of the completely different anatomical circumstances in the area of the descending aorta, however, a stent of this design cannot be used for treating aneurysms in the area of the descending aorta.

In cases of aneurysms of the thoracic aorta which may extend into the aortic arch, that is to say as far as the left subclavian artery (arteria subclavia sinistra), the problem is that the proximal fixing and sealing surface area available for the stents is not sufficient. In other words, the known stent cannot be sufficiently fixed in the aortic arch in the area opposite and proximal to the origin of the left subclavian artery.

In such a case, vascular surgery is therefore required prior to the intraluminal implantation of a vascular endoprosthesis, that is to say of a corresponding stent. Before the stent is implanted, a surgical vascular connection is created between the left subclavian artery and the common carotid artery branching off from the aortic arch proximal to the left subclavian artery, such that the subclavian artery is supplied as it were via the common carotid artery. The origin of the subclavian artery from the aortic arch can then be covered and closed off by a vascular endoprosthesis without any problem in order to ensure a sufficient surface area for fixing and sealing on the inside wall of the aorta.

Vascular surgery of this kind is very time-consuming and, in addition, the patient has to be linked up to a heart-lung machine and the body temperature of the patient has to be greatly reduced. For this reason, the mortality rate in interventions of this kind is very high.

A further disadvantage is to be seen in the fact that emergency management of a patient with an aneurysm of the thoracic aorta by insertion of a stent via a minimally invasive route has hitherto been virtually impossible, because sufficiently secure fixing of the proximal end of the stent entails problems.

DISCLOSURE OF THE INVENTION

Against this background, an object of the present invention is to create a stent which is of the kind mentioned in the introduction and which can be positioned with its proximal end in the region of the aortic arch.

According to one aspect, this object is achieved by a stent for implantation in a blood vessel comprising rings which are disposed successively in its longitudinal direction and which are made up of meandering circumferential supports, and comprising a prosthesis material which is fixed to the rings and which connects them, said prosthesis material forming a hollow cylindrical body with a jacket which is substantially closed on the circumference thereof, wherein at least one connecting support is provided between the last ring and the penultimate ring at the proximal end of the stent and connects these two rings to one another.

Owing to the new concept, stents with a jacket of prosthesis material are also suitable for implantation in the descending aorta if a connecting support is provided only between the last ring and the penultimate ring and connects these two rings to one another. In the stent disclosed in DE 100 65 824 and suitable for implantation in the ascending aorta, the distal end of the stent lying in the aortic arch is beveled and, if appropriate, has open meshes in order to guarantee supply to the arteries of the head. A mesh-type stent of this kind is not suitable for treatment of aneurysms in the region of the descending aorta. Although a simple beveling at the proximal end of the stent lying in the aortic arch also permits supply of blood to the branching-off arteries, it does not permit sufficient fixing. By contrast, the connecting support now makes it possible, for example, to omit part of the circumferential surface between the last ring and the penultimate ring or to provide the jacket with holes, such that the supply of blood to the branching-off arteries of the head is guaranteed. On the other hand, both the last ring and also the connecting supports ensure that the proximal end of the novel stent is fixed securely in the aortic arch.

In a preferred embodiment, a jacket area substantially free of prosthesis material is braced between the last ring and the penultimate ring in the area of the connecting support, in which case the connecting support is preferably V-shaped, and, further preferably, the jacket area substantially free of prosthesis material widens in a wedge shape toward the proximal end of the stent.

An advantage of this embodiment is that it is not the entire jacket area between the last ring and the penultimate ring that is designed without prosthesis material. This makes it possible, on the inside wall of the aortic arch directed away from the origins of the arteries of the head, to provide prosthesis material and thus a jacket area which is used not only for support purposes but also as a sealing surface. By means of the V-shaped design of the connecting support, it is particularly easy to produce the jacket area free of prosthesis material and widening in a wedge shape toward the proximal end of the stent. The jacket is removed in the area of the wedge-shaped jacket area, and the resulting edges of the prosthesis material are affixed to the V-shaped struts of the connecting support.

Whereas, in the distal area of the novel stent, the individual rings are connected to one another only via the jacket, that is to say the prosthesis material, the connection between the last ring and the penultimate ring is effected, on the one hand, likewise via the jacket but, on the other hand, also via the connecting support. The connecting support ensures that, despite the partially removed jacket, the last ring at the proximal end is securely connected to the rest of the hollow cylindrical body of the stent.

In another preferred embodiment the supports have a Z-shaped profile with pointed arches pointing alternately toward the proximal end and distal end of the stent, which pointed arches are connected to one another by support portions extending obliquely with respect to the longitudinal direction.

In this way, a stent structure is created which exerts a sufficient radial pressure in order to anchor itself in the vessel areas lying proximal and distal to the aneurysm, while on the other hand the stent is able to withstand the pressure of the blood flowing through it.

In a further embodiment, the proximal pointed arches of the last ring are spaced apart from the proximal pointed arches of the penultimate ring by a distance which is greater than the distance between the proximal pointed arches of the penultimate ring and the proximal pointed arches of the third last ring.

In other words, the last ring is spaced apart from the penultimate ring by a distance greater than that between the other rings in the stent.

This has the advantage that the stent can more easily adapt at its proximal end to the curvature in the aortic arch. This is of course already made possible on the one hand by the jacket area substantially free of prosthesis material, but the greater distance between the rings at the proximal end means that the stiffness here is determined to a greater extent by the remaining prosthesis material than is the case in the rest of the stent, which fact permits improved flexibility.

In another embodiment, the proximal pointed arches of the last ring are spaced apart from the distal pointed arches of the penultimate ring by a distance which is greater than the distance between the origin of the left subclavian artery and the origin of the common carotid artery from the aortic arch.

The advantage of this embodiment is that the proximal pointed arches of the last ring can bear against the inside wall of the aortic arch in a position proximal to the common carotid artery, while the distal pointed arches of the penultimate ring bear against the inside wall of the aorta in a position distal to the left subclavian artery. This ensures a secure anchoring of the proximal end of the novel stent in the aortic arch, while at the same time preventing too great a pressure being exerted on the inside wall of the aorta in the area of the origins of the common carotid artery and left subclavian artery. Moreover, this construction means that the jacket area substantially free of prosthesis material can be chosen such that the origins of the common carotid artery and left subclavian artery are not covered over by prosthesis material.

In a further embodiment, a pointed arch of the penultimate ring pointing toward the distal end of the stent is in contact with a pointed arch of a connecting support, the pointed arch of the penultimate ring pointing toward the distal end of the stent preferably being formed at least partially by the pointed arch of the connecting support.

An advantage of this embodiment is that the Z-shaped profile of the penultimate ring is not altered by the connecting support, and instead the connecting support fits into the normal structure of the ring. The distal pointed arch of the penultimate ring can be partially omitted, and the resulting gap is filled by the pointed arch of the connecting support.

In yet another embodiment, the connecting support has two legs which at their proximal end are each in contact with a support portion of the last ring.

An advantage here is that also the Z-shaped profile of the last ring does not have to be altered by the connection to the connecting support.

In a further embodiment, the connecting support has two legs which at their distal end are each in contact with a support portion of the penultimate ring.

As has already been mentioned, this embodiment has advantages in terms of construction, since the Z-shaped profile of the last ring and of the penultimate ring is not disturbed.

A further advantage is that, by virtue of this structure, a pressure on the last ring causes the V-shaped connecting support to spread outward such that the prosthesis material affixed there is pressed outward onto the inside wall of the aorta and thus closes the blood stream off from the aneurysm volume. That area of the support of the last proximal ring not covered by prosthesis material thus ensures that the proximal end of the prosthesis covered by prosthesis material is able to bend along the torus-shaped inside wall of the aorta, that the wedge-shaped, uncovered area is spread open opposite the supraaortic origins of the vessels, and that the legs of the connecting support are forced open to close the blood stream off from the aneurysm volume.

In the above embodiments of the stent according to the invention, the number of pointed arches of the last ring can be equal to that of the penultimate ring.

On the other hand, in further embodiments, the number of pointed arches of the last ring is smaller than the number of pointed arches of the penultimate ring.

The stent, or the distribution of the pointed arches in the last ring of the stent, can be configured, for example, in such a way that no free distal pointed arch is present in the jacket area which is substantially free of prosthesis material and braced in the area of the connecting support. In this way, the stent in this embodiment cannot get caught in the vessel walls during withdrawal in the distal direction.

This embodiment can also be configured, for example, in such a way that, in the last ring, no distal pointed arch is present at that location which corresponds to or lies opposite the pointed arch of the penultimate ring pointing toward the distal end of the stent, formed at least partially by the pointed arch of the connecting support.

In once again another embodiment, at least two further connecting supports are provided which, with their proximal end, are each in contact with a support portion of the last ring and which, with their distal end, are each in contact with a support portion of the penultimate ring.

In another embodiment, the two further connecting supports intersect at a point.

By means of the further connecting supports in these embodiments, the flank stability and the flank leaktightness can be advantageously enhanced.

These embodiments also have the advantage of improving the stability of the stent especially in the distal area, as a result of which it is again possible to avoid the problem of the pointed arches becoming caught during withdrawal of the stent in the distal direction.

In another embodiment, the last ring and the connecting support are formed integrally with one another.

This embodiment is of advantage in construction terms, since all that has to be done is to bend a customary Z-shaped ring and then extend one of the free ends in the direction of the distal area, turn it back there and guide it back to the last ring.

In yet another embodiment, the respective support portion of the last ring or penultimate ring and a portion of the connecting support resting on said supporting portion are connected to one another by a crimp sleeve.

This embodiment is of advantage in construction terms, since the wire areas bearing on one another are crimped together in this way. However, this measure is also advantageous from the point of view of safety, since the free ends both of the penultimate ring and also of the last ring are in this way covered by the crimp sleeves, such that injury to the inside wall of the aorta is avoided.

In a further embodiment, the pointed arches of the last ring which point toward the proximal end of the stent are bent outward in relation to its pointed arches pointing toward the distal end of the stent.

The advantage of this embodiment is that the proximal pointed arches fit the inside wall of the aortic arch, which inside wall can be likened with good approximation to the inner surface of a segment of a torus. At the same time, through the elasticity of the wire material, the outwardly bent pointed arches generate a pressure on the wall of the aorta so as to ensure the fixing and positioning and the sealing action of the vascular endoprosthesis or stent.

Further, in another embodiment, the supports and the connecting support are made of a wire-like, elastic material.

This measure is known per se and ensures that the stent can initially be compressed, such that its external diameter decreases, for insertion into the lumen of the aorta. After release of the stent, the latter expands and anchors itself in the corresponding blood vessel.

In another embodiment, a distal marker is disposed on the jacket at a position in the distal direction from a distal pointed arch of the connecting support, and in this case it is further preferable if a proximal marker is disposed on the jacket at a position in the distal direction from a support portion of the last ring, the markers preferably being X-ray markers.

This embodiment has the advantage of creating a positioning aid with which it is possible to monitor the current position of the stent during implantation and also to check the position of the jacket area substantially free of prosthesis material relative to the supraaortic origins after implantation.

In yet another embodiment, the prosthesis material is composed of a textile material or of film, and it is in this case further preferable if the prosthesis material is fixed on the supports and on the connecting support by sewing, gluing or melting in.

These measures are known from the prior art; they permit rapid and inexpensive but reliable production of the novel stent.

Further advantages and features will become evident from the following description and from the attached drawing.

It goes without saying that the aforementioned features and those still to be explained below can be used not only in the respectively cited combination but also in other combinations or in isolation, without departing from the scope of the present invention.

BRIEF DESCRIPTION OF THE DRAWINGS

An embodiment of the invention is depicted in the drawing and is described in greater detail below with reference to this drawing, in which.

MODES OF CARRYING OUT THE INVENTION

Figure 1:
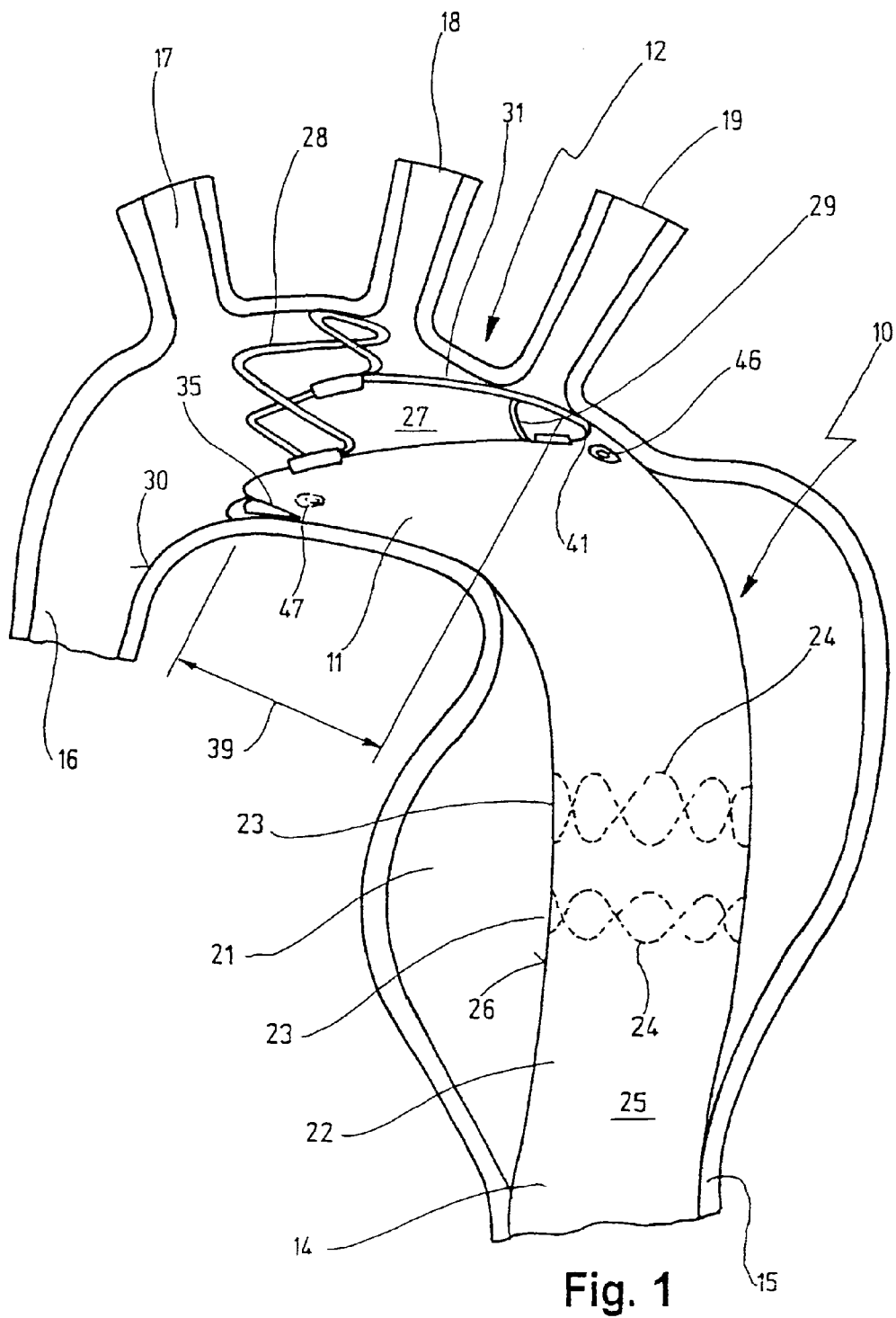
FIG. 1 shows a schematic representation of an embodiment of an endovascular stent implanted in the descending branch of the aorta.

In FIG. 1, reference number 10 designates a stent which is anchored with its proximal end 11 in the aortic arch 12 and with its distal end 14 in the descending aorta 15.

Before the stent 10 is described in detail, the aortic system also shown schematically in FIG. 1 will first be explained.

The ascending branch 16 of the aorta (aorta ascendens) is connected, via the aortic sinus (not shown in FIG. 1), to the left ventricle of the heart (also not shown in FIG. 1). The ascending aorta 16 is connected to the descending aorta 15 via the aortic arch 12. Arterial vessels of the head have their origin in the region of the aortic arch 12, namely the brachiocephalic trunk 17, the common carotid artery 18 and the left subclavian artery 19.

Reference number 21 designates an aneurysm located in the descending aorta 15 and bridged, as it were, by the stent 10. The blood flow from the ascending aorta 16 passes through the aortic arch 12 into the proximal end 11 of the stent 10 and leaves the latter at the distal end 14. For this purpose, the stent 10 has a hollow cylindrical body 22 formed by rings 23 of meandering supports 24 which are indicated schematically in FIG. 1 and which are connected to one another by prosthesis material 25. The prosthesis material 25 is in a known manner a textile material or a film and is fixed to the supports 24 by sewing, gluing or melting in.

In this way, the passage through the stent is kept open so that the hollow cylindrical body 22 forms.

At its proximal end 11, the stent 10 has a wedge-shaped free jacket area 27 which widens toward the proximal end 11 and which is braced between a last proximal ring 28, a penultimate proximal ring 29 and a connecting support 31 which connects the last ring 28 to the penultimate ring 29.

This jacket area 27 substantially free of prosthesis material 25 means that blood conveyed from the ascending aorta 16 can pass into the common carotid artery 18 and the left subclavian artery 19. Outside the free jacket area 27, however, prosthesis material 25 is present between the last ring 28 and the penultimate ring 29, such that the stent 10 bears with its proximal end tightly on the inside wall 30 of the aorta. This prevents blood from passing between the stent 10 and the inside wall 30 of the aorta into the area of the aneurysm 21, possibly widening the latter and finally leading to a rupture.

Figure 2:
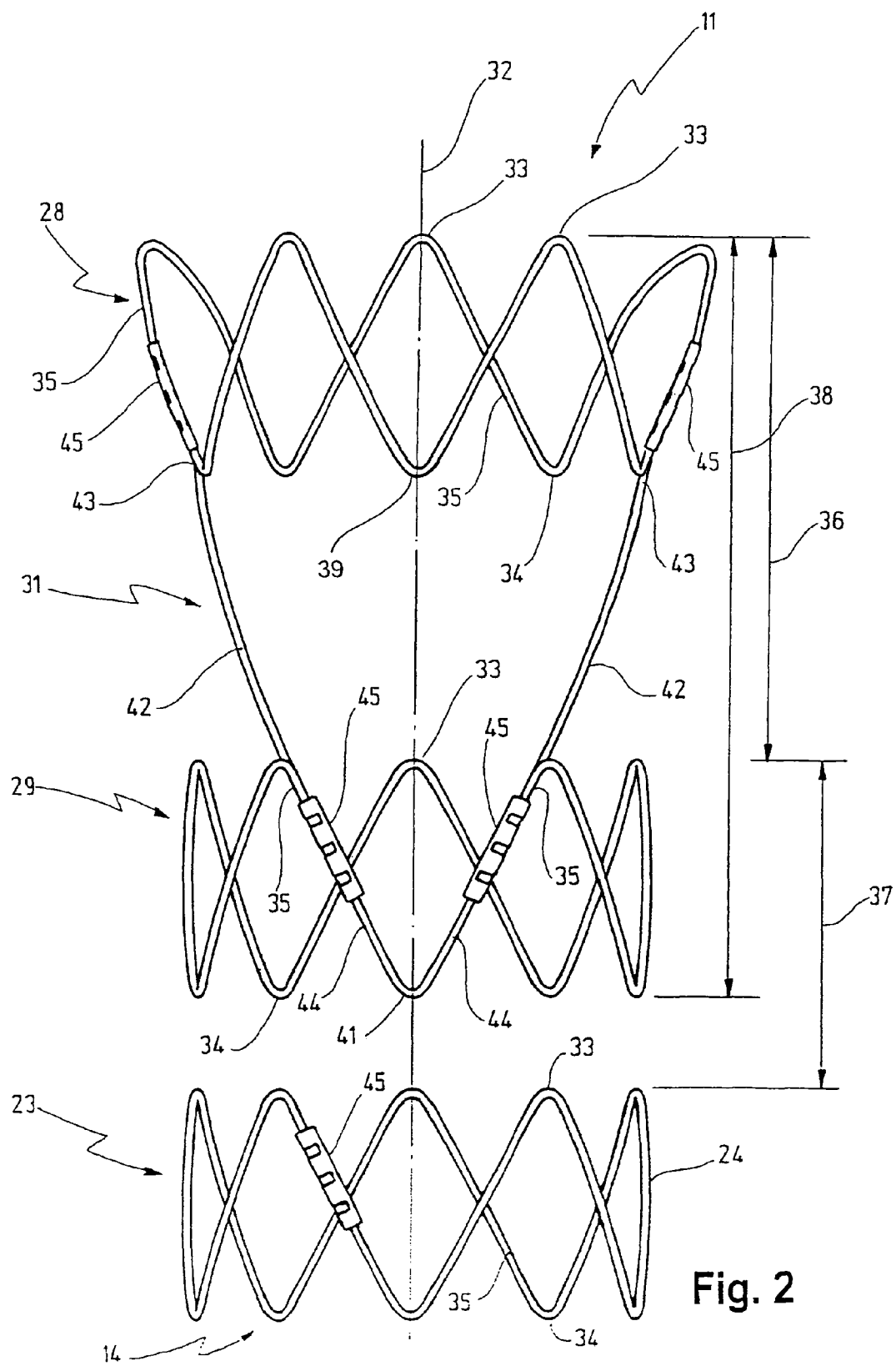
FIG. 2 shows the support structure for the stent from FIG. 1, but without the surrounding jacket.

The structure of the stent 10 from FIG. 1 is shown in more detail in the schematic side view in FIG. 2; for the sake of clarity, the prosthesis material 25 has been omitted in FIG. 2.

It will first be noted that the last ring 28, the penultimate ring 29 and further rings 23 are disposed in succession in the longitudinal direction 32, only one of said further rings being shown here. Each of these rings 23, 28, 29 has several proximal pointed arches 33 and distal pointed arches 34 which are connected to one another by support portions 35 that extend obliquely with respect to the longitudinal direction 32. The rings 23, 28, 29 made up of meandering circumferential supports 24 are formed in this way. It will be noted that the supports 24 and also the connecting support 31 are made of a wire-like elastic material.

The proximal pointed arches 33 of the last ring 28 are spaced apart from the proximal pointed arches 33 of the penultimate ring 29 by a distance designated by 36 which is greater than the distance 37 between the proximal pointed arches 33 of the penultimate ring 29 and the proximal pointed arches 33 of the third last ring 23. In this way, the stent 10 is more flexible and movable at its proximal end 11 than in the direction of its distal end 14.

Moreover, the proximal pointed arches 33 of the last ring 28 are spaced apart from the distal pointed arches 34 of the penultimate ring 29 by a distance 38 which is greater than the distance 39 indicated in FIG. 1 between the origin of the left subclavian artery 19 and the origin of the common carotid artery 18 from the aortic arch 12. In this way, the last proximal ring 28 can brace itself proximally from the common carotid artery on the inside wall 30 of the aorta, whereas the penultimate ring 29 can brace itself distally from the left subclavian artery and can there press the prosthesis material 25 about the entire circumference against the inside wall 30 of the aorta.

The V-shaped connecting support 31 which connects the last ring 28 and the penultimate ring 29 to one another has a distal pointed arch 41 and two legs 42 which adjoin the pointed arch 41 and which widen in a V shape to the distal end 11 of the stent 10. The proximal ends 43 of the legs 42 are in contact with support portions 35 of the last ring 28. The distal ends 44 of the legs 42 are in contact with corresponding support portions 35 of the penultimate ring 29. The connection between the support portions 35 and the respective ends 43, 44 of the legs 42 is effected by crimp sleeves 45 which also close the meandering supports 24, for example of the ring 23, to give its Z-shaped profile.

Figure 3:
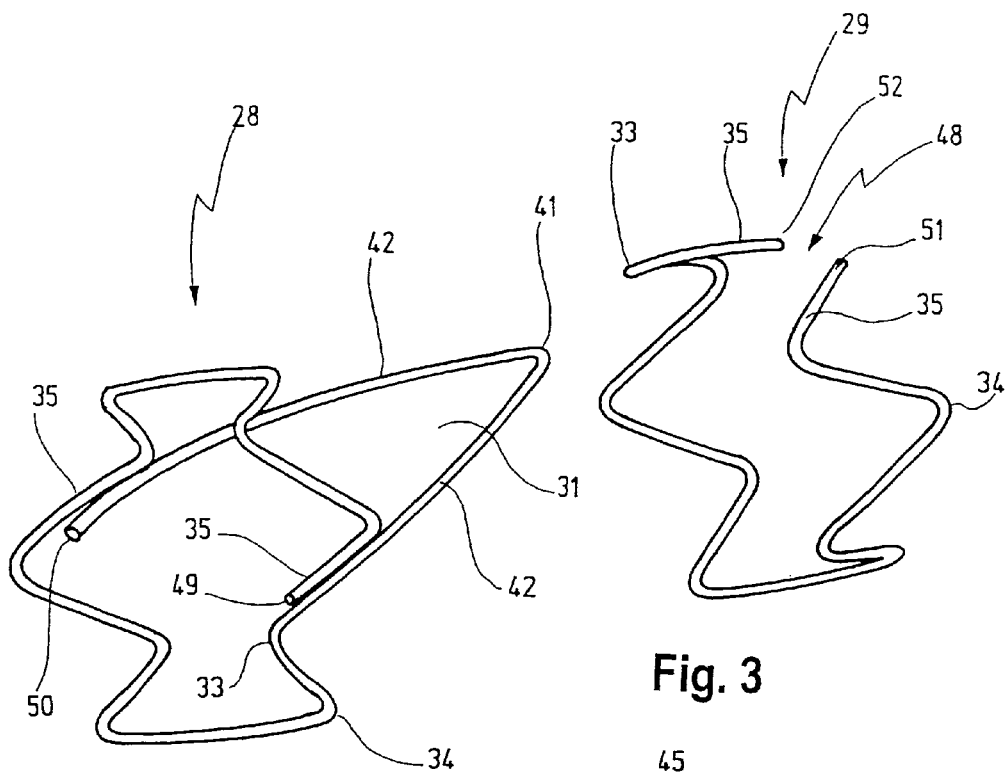
FIG. 3 shows the last and penultimate proximal rings of the stent from FIG. 2, not yet connected to one another.

FIG. 3 shows the last ring 28 and the penultimate ring 29 directly after production, that is to say before they are connected to one another.

It will be seen from the left half of FIG. 3 that the last ring 28 and the connecting support 31 are formed integrally with one another. Moreover, it will be seen from the right half of FIG. 3 that the penultimate ring 29 is, as it were, missing a distal pointed arch 34, which fact is indicated by a gap designated by 48. This gap is now filled by the distal pointed arch 41 of the connecting support 31.

The last ring 28 is formed, starting at its free end 49, by bending the corresponding wire material in a number of Z-shapes so that the proximal and distal pointed arch 33 and 34 form. When the ring 28 is closed, the wire material is continued further in the distal direction and is bent at the distal pointed arch 41 and returned to the support portion 35 where the wire is cut off so as to obtain the second free end 50 of the one-piece structure, which represents both the last ring 28 and also the connecting support 31. The penultimate ring 29 correspondingly has two free ends 51 and 52 which lie on both sides of the gap 48.

Figure 4:
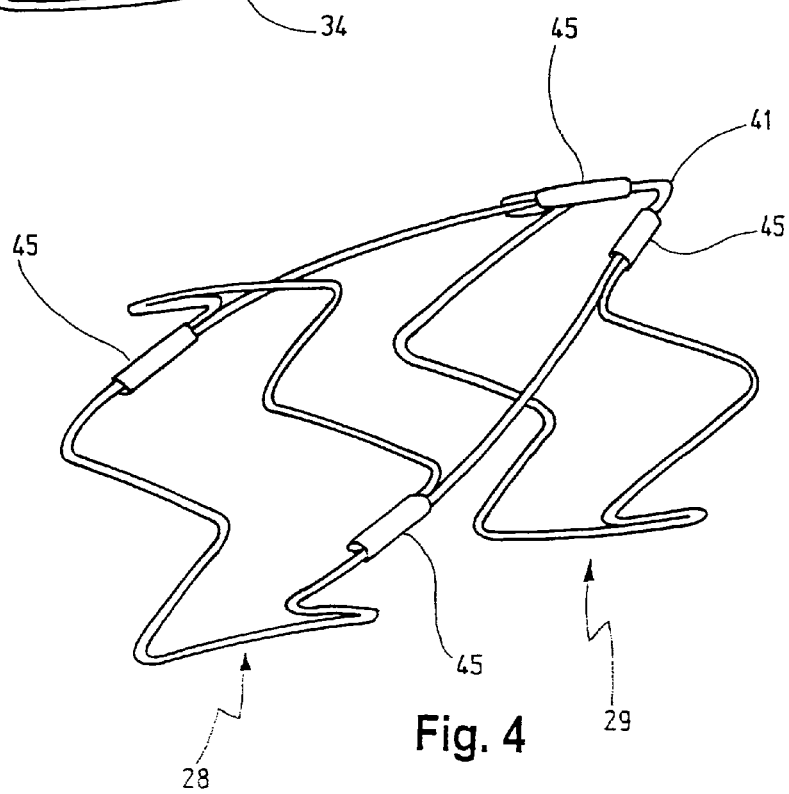
FIG. 4 shows the two rings from FIG. 3, but now connected to one another by crimp sleeves.

The last ring 28 and the penultimate ring 29 are now joined together, as is shown in FIG. 4, a crimp sleeve 45 being in each case pushed onto the free ends 49 to 52, which crimp sleeve on the one hand connects the leg 42 to the corresponding support portions 35 and on the other hand covers the free ends 49 to 52 so that damage to the inside wall of the aorta is avoided.

The last ring 28 and the penultimate ring 29 form, together with the connecting support 31, a fixing structure which is provided at the proximal end 11 of the stent 10. With this fixing structure, the inside wall of the aorta lying opposite and proximally from the origin of the left subclavian artery can now also be utilized as a fixing and sealing surface, without this origin being closed off. When the new stent is implanted in the region for which it is intended, it is now no longer necessary to first perform an onerous service intervention.

It will also be noted that the proximal pointed arches 33 of the last ring 28 are widened outward or curved outward relative to the distal pointed arches 34, as can be seen at the top of FIG. 2. In this way, the pointed arches 33 bear on the inside wall 30 of the aorta and at the same time generate, through the elasticity of the wire material, a pressure on the inside wall 30 of the aorta that ensures the fixing and positioning and also the sealing of the vascular endoprosthesis.

It will also be seen from FIG. 1 that the last ring 28 can be bent forward, as a result of which the legs 42 of the connecting support 31 spread outward and bear tightly on the inside wall 30 of the aorta. This is further assisted by the pressure exerted by the inside wall of the aorta on the last ring 28, which likewise spreads the legs 42 of the connecting support 31 outward. In this way, the prosthesis material fixed there is pressed outward onto the inside wall 30 of the aorta and thus seals the blood stream off from the volume of the aneurysm 21.

The wedge-shaped area 27 remaining free of prosthesis material 25 ensures supply of the left subclavian artery 19 and common carotid artery 18.

As a positioning aid during implantation, and for checking the location of the uncovered prosthesis area, that is to say of the free jacket area 27, relative to the supraaortic origins 19 and 18 after implantation, two X-ray markers 46 and 47 are provided, shown in FIG. 1. The marker 46 is a distal marker which is arranged in the distal direction from the distal pointed arch 41 of the connecting support 31. The marker 47 is, by contrast, a proximal marker which is secured on the jacket 26 in the distal direction from a support portion of the last ring 28.

Figure 5:
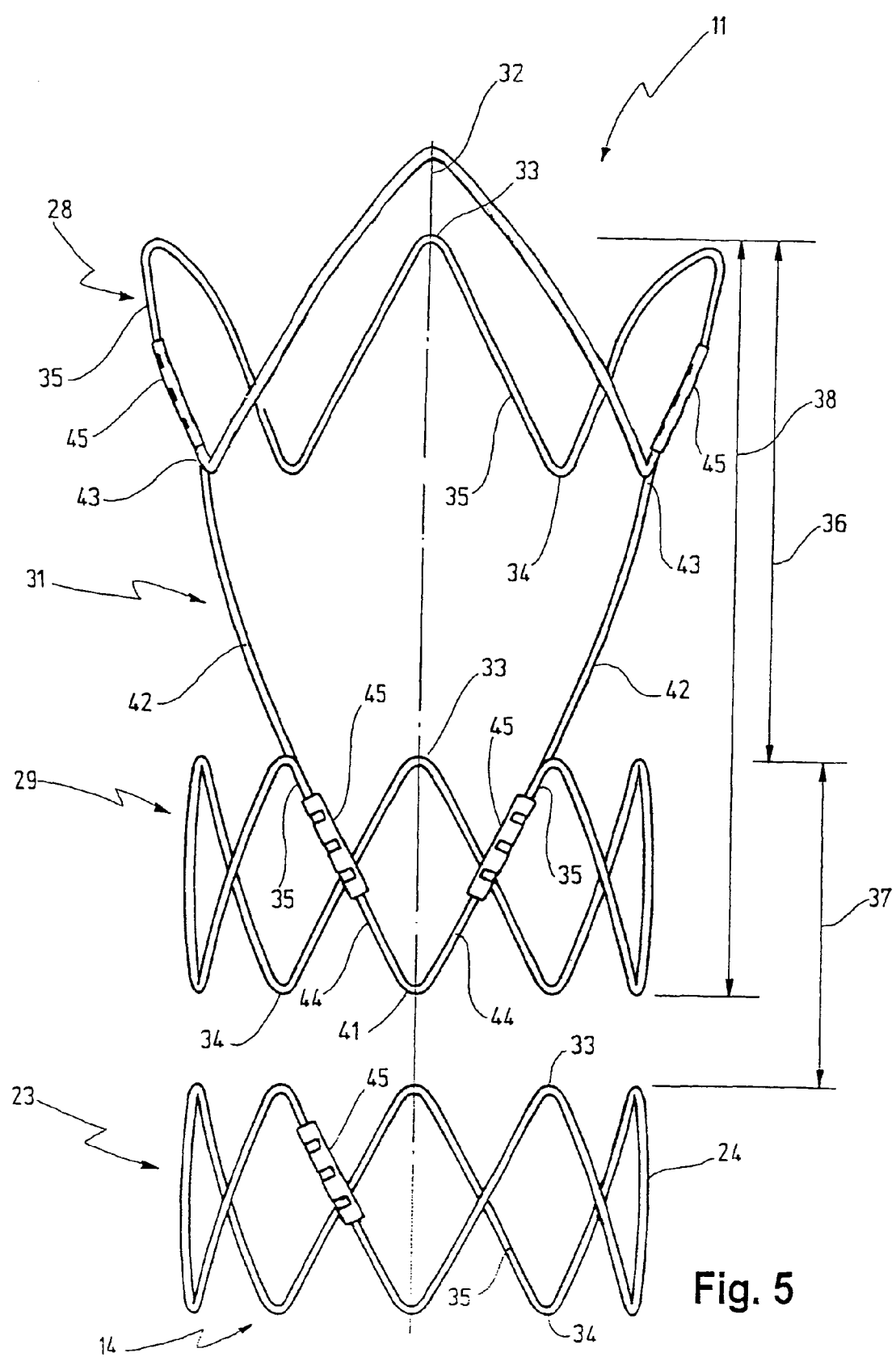
FIG. 5 shows a further embodiment of the stent according to the invention without surrounding jacket.

A further embodiment of the stent according to the invention is shown in a schematic side view in FIG. 5 where, as in FIG. 2, the prosthesis material 25 has been omitted for the sake of clarity. In FIGS. 5 through 9a, the same reference numbers as in FIG. 2 have been used to identify the same elements of the stents.

It will be seen from FIG. 5 that, in this embodiment too, the last ring 28, the penultimate ring 29 and further rings 23 are arranged in succession in the longitudinal direction 32, only one of said further rings 23 being shown. It will also be seen that the last ring 28 has one proximal pointed arch 33, and therefore also one distal pointed arch 34, less than the penultimate ring 29 and the ring 23. In this embodiment, therefore, in comparison to FIG. 2, the distal pointed arch 39 is absent (see FIG. 2).

Figure 6:
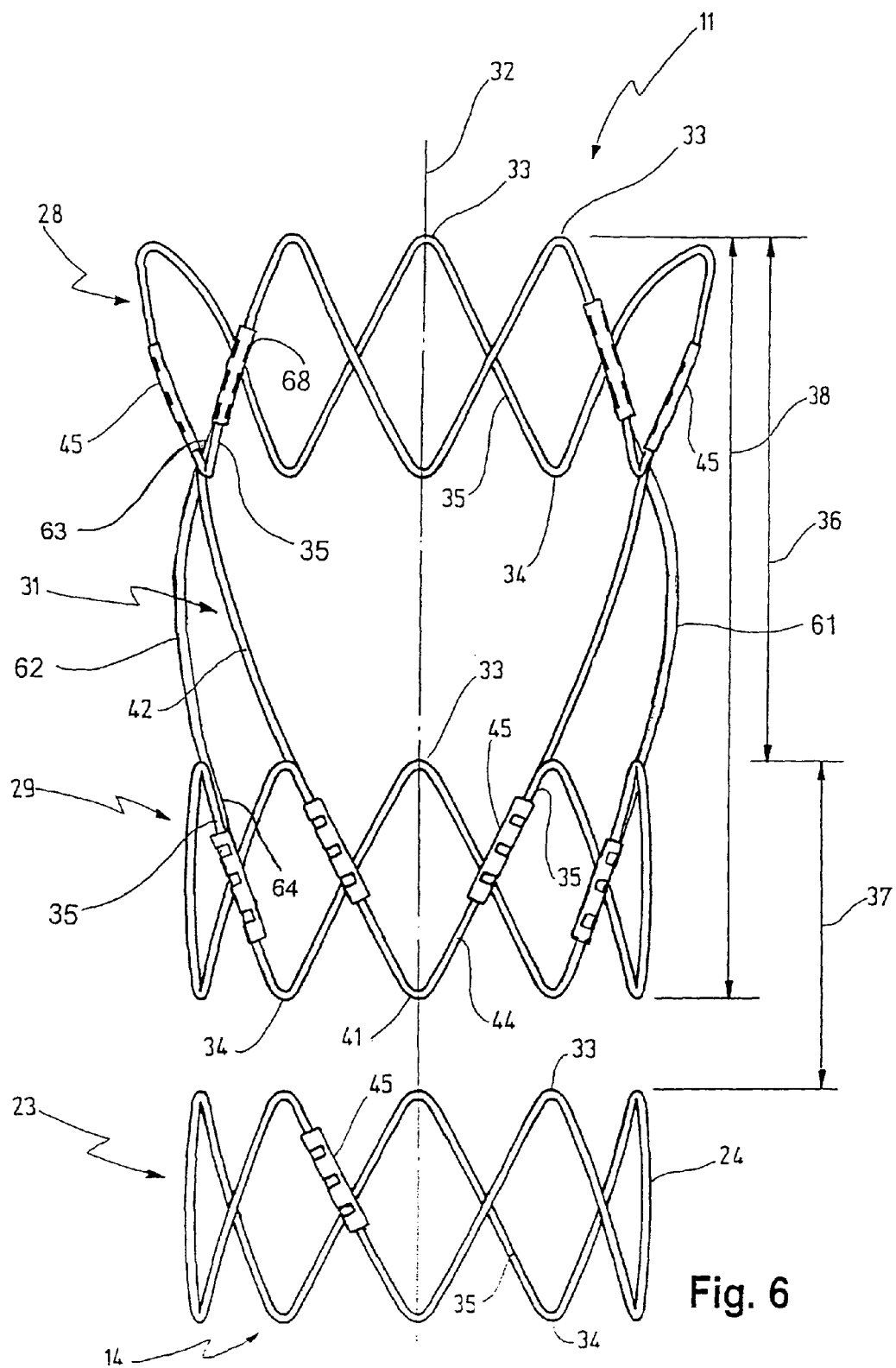
FIG. 6 shows yet another embodiment of the stent according to the invention with additional connecting supports, likewise without surrounding jacket.

FIG. 6 shows a further embodiment of the stent according to the invention, this embodiment having additional connecting supports 61 and 62 compared to the embodiment from FIG. 2. The proximal end 63 of the connecting supports 61 and 62 is in each case brought into contact with a support portion 35 of the last ring 28, and their distal end 64 is in each case brought into contact with a support portion 35 of the penultimate ring 29. It will be seen from FIG. 6 that, in this way, the additional connecting supports 61 and 62 constitute a kind of flank reinforcement for the stent.

Figure 7A:
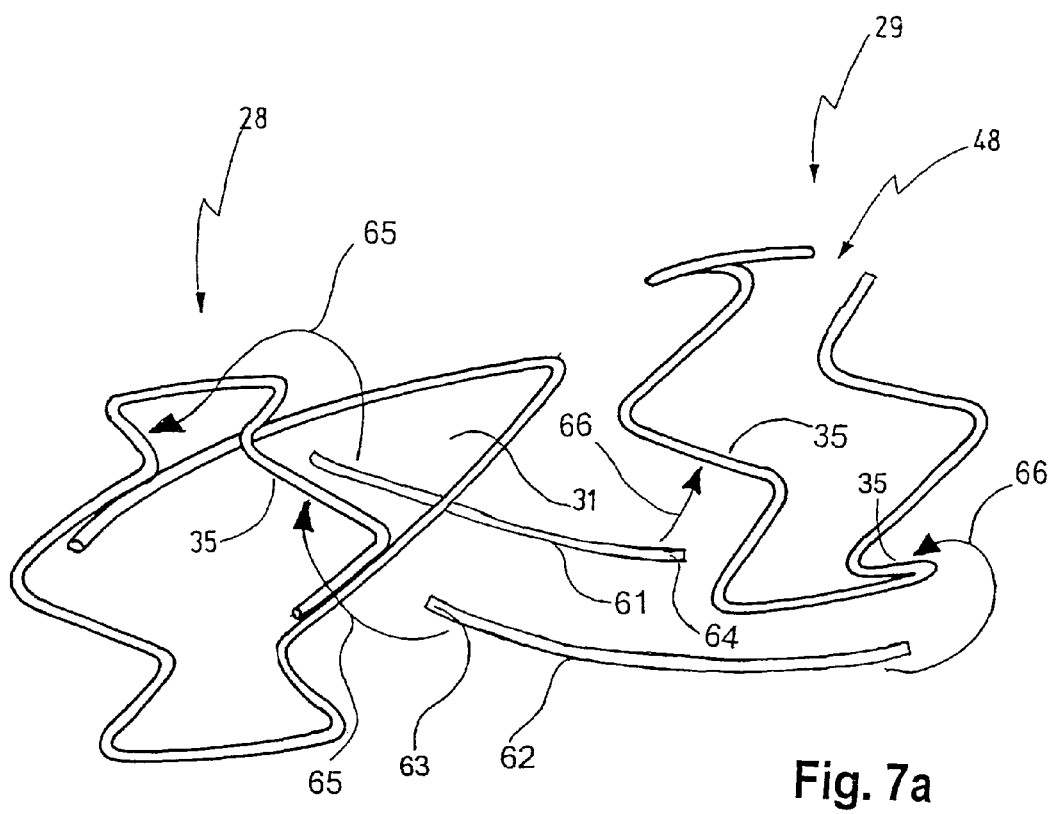
FIG. 7*a* shows the last and penultimate proximal rings of the stent from FIG. 6, with the connecting supports that are to be applied, and not yet connected to one another.

FIG. 7a shows the last ring 28 and the penultimate ring 29 directly after production, that is to say before they are connected to one another. In FIG. 7a, as in FIG. 3, it will be seen that the last ring 28 and the connecting support 31 are formed integrally with one another. The proximal end 63 of the additional connecting supports 61 and 62 is brought into contact with a support portion 35 of the last ring 28, as is indicated by the arrows 65, and the distal ends 64 are in each case brought into contact with a support portion 35 of the penultimate ring 29, as is indicated by the arrows 66.

Figure 7B:
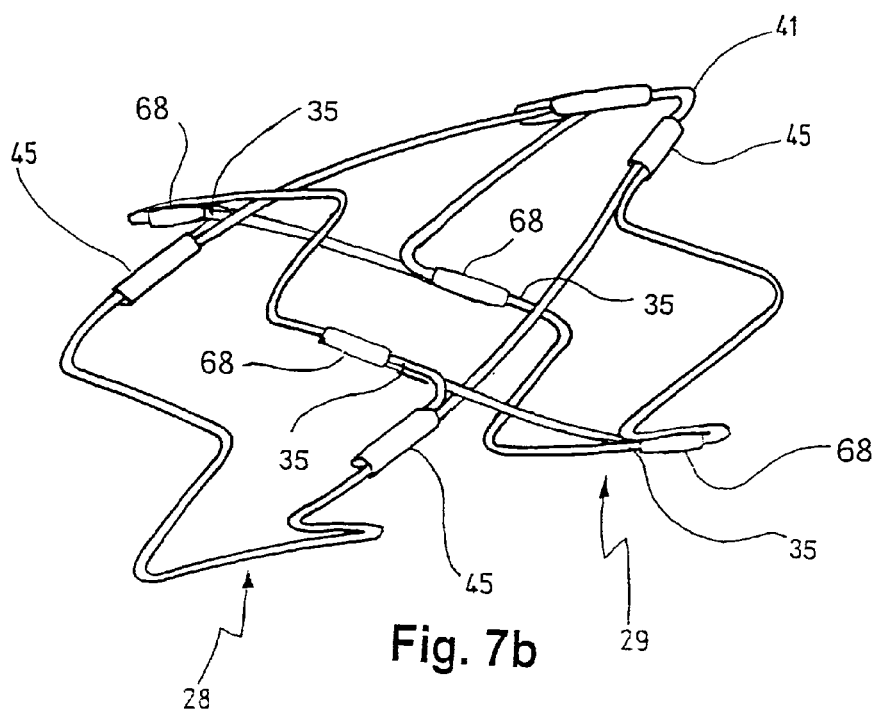
FIG. 7*b* shows the two rings from FIG. 7*a*, now connected to one another by crimp sleeves.

It will be seen from FIG. 7b that the two rings 28 and 29 are joined together, the ends in each case being connected via crimp sleeves 68 to the corresponding support portions 35, so that damage to the inside wall of the aorta is avoided.

Figure 8:
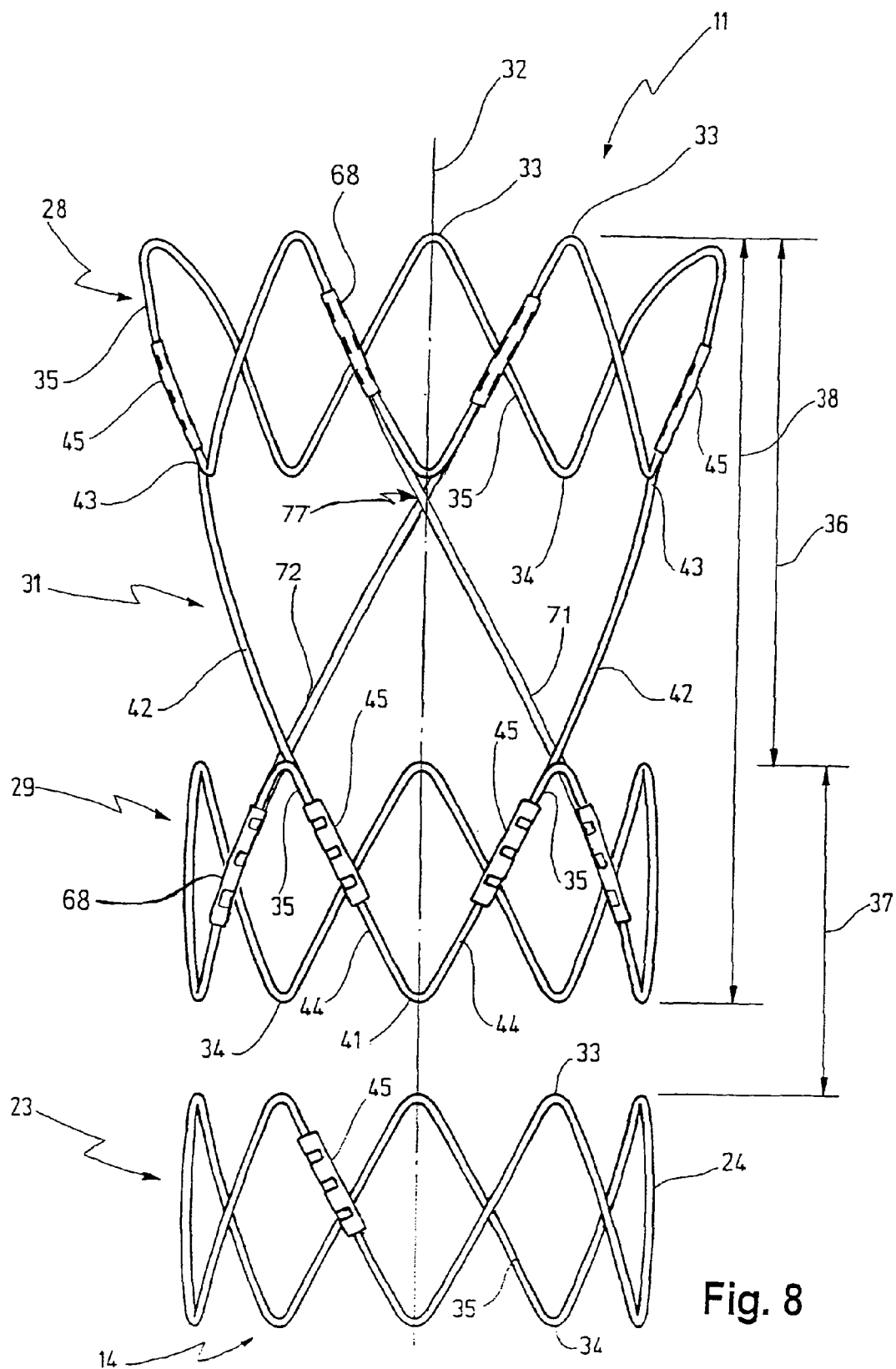
FIG. 8 again shows a further embodiment of the stent according to the invention with intersecting additional connecting supports, without surrounding jacket.

FIG. 8 shows another embodiment of the stent according to the invention where, as in FIG. 6, two additional connecting supports 71 and 72 are provided, but these ones intersect at a point 77.

Figure 9A:
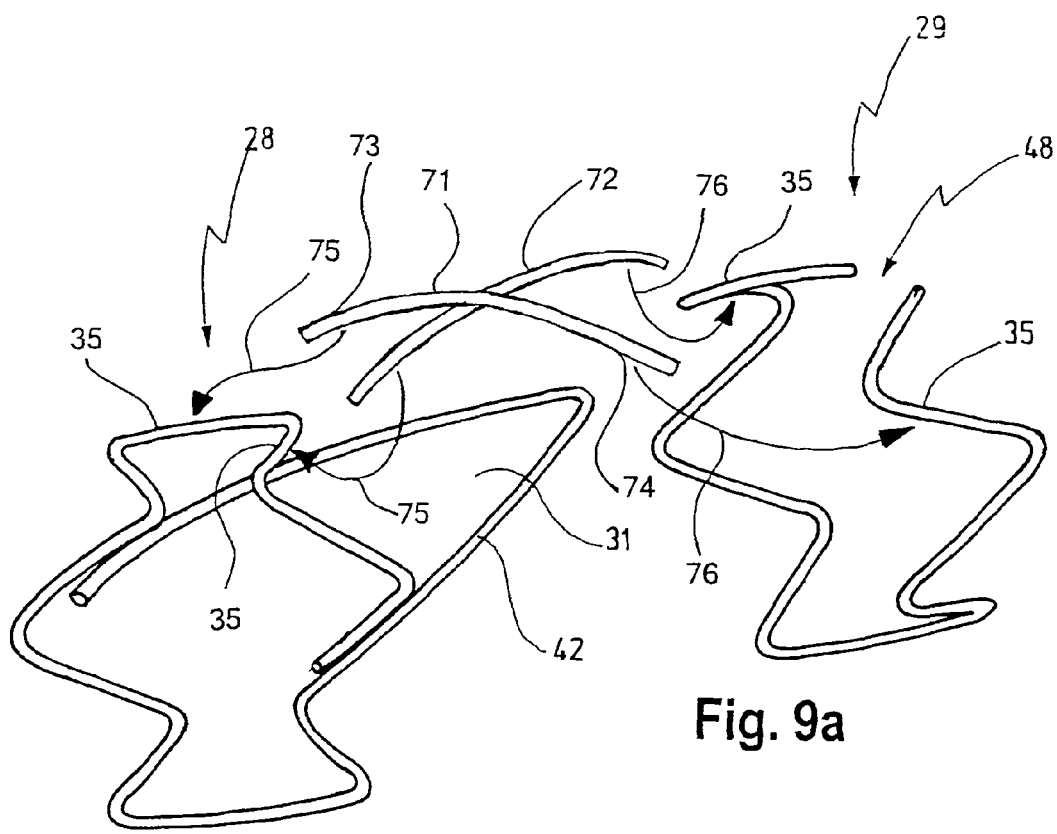
FIG. 9*a* shows the last and penultimate proximal rings of the stent from FIG. 8, with the intersecting connecting supports that are to be applied, but before being connected to one another.

Similarly to the situation in FIG. 7a, it will be seen from FIG. 9a that the intersecting connecting supports 71 and 72 are in each case brought into contact with a support portion 35 of the last ring 28 via their respective proximal end 73, as is indicated by the arrows 75, and their distal end 74 is brought into contact with a support portion 35 of the penultimate ring 29, as is indicated by the arrows 76.

Figure 9B:
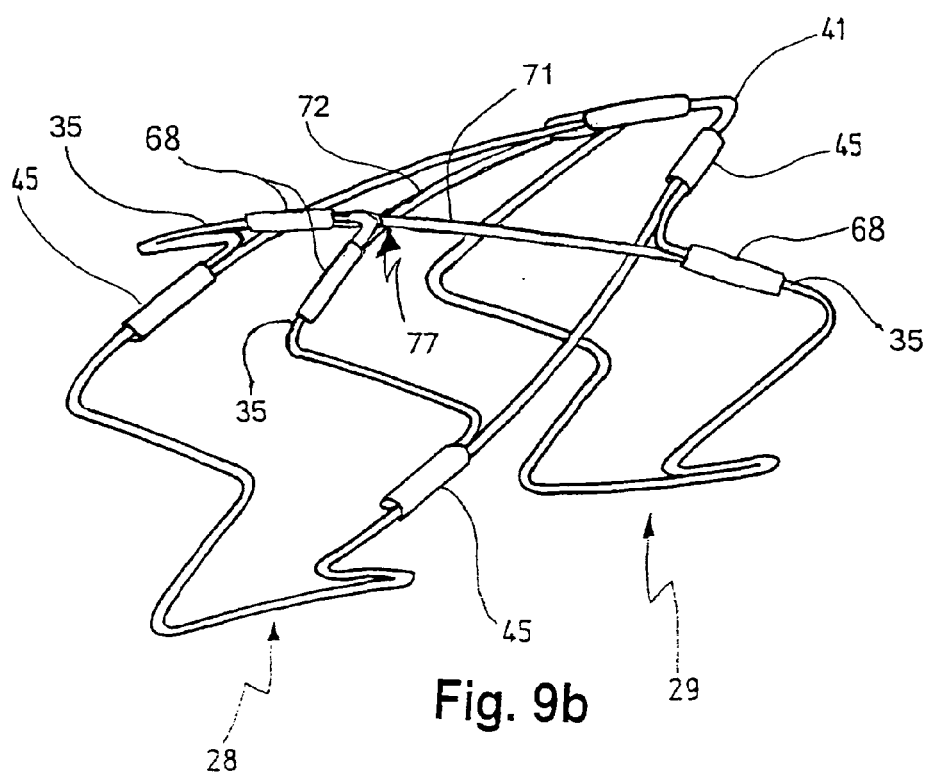
FIG. 9*b* shows the two rings from FIG. 9*a*, now connected to one another by crimp sleeves.

It will be seen from FIG. 9b that the two rings 28 and 29 are joined together, the ends of the connecting supports 71 and 72 being connected, by application of crimp sleeves 68, to the respective support portions 35 of the last ring 28 and of the penultimate ring 29.

The invention claimed is:

1. A stent for implantation in a blood vessel, said stent having a proximal end and a distal end and comprising a plurality of rings, which are disposed successively in the stent's longitudinal direction and which are made up of meandering circumferential supports, and further comprising a prosthesis material which is fixed to the rings and which connects them, said prosthesis material and said rings forming a hollow cylindrical body, the hollow cylindrical body having a circumference and forming a jacket which is substantially closed on the circumference and further comprising a last ring, a penultimate ring and a third last ring at the proximal end, wherein only between the last ring and the penultimate ring at the proximal end of the stent one V-shaped connecting support is provided and connects the last and penultimate rings to one another, and wherein apart from the last ring and the penultimate ring, which are connected via the V-shaped connecting support, the rings are only connected to one another by said prosthesis material, and wherein an area free of prosthesis material is braced between the last ring and the penultimate ring only in the area of the V-shaped connecting support.

2. The stent as claimed in claim 1, wherein the area substantially free of prosthesis material widens in a wedge shape toward the proximal end of the stent.

3. The stent as claimed in claim 1, wherein the circumferential supports have a Z-shaped profile with pointed arches pointing alternately toward the proximal end and distal end of the stent, wherein the pointed arches are connected to one another by support portions extending obliquely with respect to the longitudinal direction.

4. The stent as claimed in claim 3, wherein the proximal pointed arches of the last ring are spaced apart from the proximal pointed arches of the penultimate ring by a distance which is greater than the distance between the proximal pointed arches of the penultimate ring and the proximal pointed arches of the third last ring.

5. The stent as claimed in claim 3, wherein a pointed arch of the penultimate ring pointing toward the distal end of the stent is in contact with a pointed arch of the connecting support.

6. The stent as claimed in claim 5, wherein the pointed arch of the penultimate ring pointing toward the distal end of the stent is formed at least partially by the pointed arch of the connecting support.

7. The stent as claimed in claim 3, wherein the connecting support has two legs which at their proximal end are each in contact with a support portion of the last ring.

8. The stent as claimed in claim 3, wherein the connecting support has two legs which at their distal end are each in contact with a support portion of the penultimate ring.

9. The stent as claimed in claim 3, wherein the number of pointed arches of the last ring is smaller than the number of pointed arches of the penultimate ring.

10. The stent as claimed in claim 3, wherein two further connecting supports are provided which, with their proximal end, are each in contact with a support portion of the last ring and which, with their distal end, are each in contact with a support portion of the penultimate ring.

11. The stent as claimed in claim 10, wherein the connecting supports are in contact via their respective proximal end and respective distal end with the support portions of the last ring and penultimate ring in such a way that the connecting supports intersect at a point.

12. The stent as claimed in claim 1, wherein the last ring and the connecting support are formed integrally with one another.

13. The stent as claimed in claim 3, wherein the respective support portion of the last ring or penultimate ring and a portion of the at least one connecting support situated in contact with said supporting portion are connected to one another by a crimp sleeve.

14. The stent as claimed in claim 3, wherein the pointed arches of the last ring which point toward the proximal end of the stent are bent outward in relation to its pointed arches pointing toward the distal end of the stent.

15. The stent as claimed in claim 1, wherein the circumferential supports and the at least one connecting support are made of a wire-like, elastic material.

16. The stent as claimed in claim 1, wherein a distal marker is disposed on the jacket at a position in the distal direction from a distal pointed arch of the connecting support.

17. The stent as claimed in claim 3, wherein a proximal marker is disposed on the jacket at a position in the distal direction from a support portion of the last ring.

18. The stent as claimed in claim 16, wherein the marker is an X-ray marker.

19. The stent as claimed in claim 1, wherein the prosthesis material is composed of a textile material or of film.

20. The stent as claimed in claim 1, wherein the prosthesis material is fixed on the circumferential supports and on the at least one connecting support by sewing, gluing or melting in.

21. A stent, comprising: a plurality of circumferential supports disposed successively in a longitudinal direction; and a prosthesis material which is fixed to at least one of the plurality of circumferential supports and which connects the plurality of circumferential supports, said prosthesis material and said circumferential supports together forming a hollow substantially cylindrical body with a jacket which is substantially closed on a circumference thereof, and further comprising a last circumferential support and a penultimate circumferential support at a proximal end of the stent, wherein only between the last circumferential support and the penultimate circumferential support at the proximal end of the stent one V-shaped connecting support is provided and connects the last and penultimate circumferential supports to one another, and wherein apart from the last circumferential support and the penultimate circumferential support, which are connected via the V-shaped connecting support, the circumferential supports are only connected to one another by said prosthesis material, and wherein an area free of prosthesis material is braced between the last circumferential support and the penultimate circumferential support only in the area of the V-shaped connecting support.

* * * * *